(12) United States Patent
Wang (10) Patent No.: US 8,916,831 B2
(45) Date of Patent: Dec. 23, 2014

(54) EUV ACTINIC RETICLE INSPECTION SYSTEM USING IMAGING SENSOR WITH THIN FILM SPECTRAL PURITY FILTER COATING

(75) Inventor: Daimian Wang, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 133 days.

(21) Appl. No.: 13/419,042

(22) Filed: Mar. 13, 2012

(65) Prior Publication Data

US 2012/0235049 A1 Sep. 20, 2012

Related U.S. Application Data

(60) Provisional application No. 61/453,493, filed on Mar. 16, 2011.

(51) Int. Cl.
*G01J 1/42* (2006.01)
*G03F 1/84* (2012.01)
*H01L 27/146* (2006.01)
*G01N 21/956* (2006.01)
*G03F 1/24* (2012.01)

(52) U.S. Cl.
CPC ............ *G03F 1/84* (2013.01); *H01L 27/14625* (2013.01); *G01N 2021/95676* (2013.01); *H01L 27/1462* (2013.01); *G03F 1/24* (2013.01); *G01N 21/956* (2013.01)
USPC ........................................................ 250/372

(58) Field of Classification Search
CPC ....................................................... G01J 1/429
USPC .......................................................... 250/372
See application file for complete search history.

(56) References Cited

U.S. PATENT DOCUMENTS

| | | | |
|---|---|---|---|
| 6,738,135 B1 * | 5/2004 | Underwood et al. | 356/237.5 |
| 6,825,988 B2 | 11/2004 | Bristol | |
| 7,372,623 B2 | 5/2008 | Banine et al. | |
| 7,598,508 B2 | 10/2009 | Sogard | |
| 7,666,555 B2 | 2/2010 | Goldstein et al. | |
| 2004/0207836 A1 * | 10/2004 | Chhibber et al. | 356/237.4 |
| 2005/0008864 A1 * | 1/2005 | Ingen Schenau et al. | 428/411.1 |
| 2006/0219931 A1 | 10/2006 | Vand Der Werf et al. | |
| 2010/0149505 A1 * | 6/2010 | Sewell et al. | 355/67 |
| 2012/0075607 A1 * | 3/2012 | Knarren et al. | 355/67 |

FOREIGN PATENT DOCUMENTS

WO WO 2010-018039 A1 2/2010
WO WO 2010-034385 A1 4/2010

* cited by examiner

*Primary Examiner* — Constantine Hannaher
(74) *Attorney, Agent, or Firm* — Suiter Swantz pc llo (57) ABSTRACT

An extreme ultraviolet (EUV) actinic reticle imaging system suitable for discharge produced plasma (DPP) or laser produced plasma (LPP) reticle imaging systems using a thin film coating spectral purity filter (SPF) positioned on or proximate to the EUV imaging sensor; an EUV imaging sensor carrying this SPF; and methods for making and using the SPF for reticle inspection. The coating may be applied to the imaging sensor in any manner suitable for the particular coating selected. The coating may be composed of a single layer or multiple layers. Typical SPF coating materials include zirconium (Zr) and silicon-zirconium (Si/Zr) in a thickness between 10 nm and 100 nm.

25 Claims, 8 Drawing Sheets

EUV ACTINIC RETICLE INSPECTION SYSTEM USING IMAGING SENSOR WITH THIN FILM SPECTRAL PURITY FILTER COATING

REFERENCE TO RELATED APPLICATIONS

This application claims priority to U.S. Provisional Patent Application Ser. No. 61/453,493, filed Mar. 16, 2011, which is incorporated herein by reference.

FIELD OF THE INVENTION

This application relates to extreme ultraviolet (EUV) lithographic integrated circuit (IC) wafer fabrication and, more particularly, an EUV actinic reticle inspection system using a thin film coating spectral purity filter (SPF) positioned on or proximate to the EUV imaging sensor.

BACKGROUND OF THE INVENTION

As the demand for smaller semiconductor features continues to increase, so too does the demand for optical-based semiconductor inspections systems capable of imaging such small features. One semiconductor processing technique developed to achieve the increased fabrication demands includes extreme ultraviolet (EUV) lithography. EUV lithographic integrated circuit (IC) fabrication involves the use of a reticle carrying a pattern mask to expose an integrated circuit into silicon wafers using EUV light, generate by a EUV source, such as discharge produced plasma source or a laser produced plasma source. In order to accommodate the corresponding demands on inspection technologies improved EUV spectral purity filters are required. Past EUV spectral purity filters include gas stream based filters, multi-layered structures disposed on mesh-like grids, pellicles disposed on mesh-like grids, and diffractive grating based filters. Each of these types of EUV spectral purity filters carries along with it a number of disadvantages, such as chemical contamination, difficulty of implementation, and lack of transmission efficiency. It is therefore desirable to produce a spectral purity filter which overcomes the deficiencies identified in previous spectral purity filters.

SUMMARY OF THE INVENTION

The present invention meets the needs described above in an extreme ultraviolet (EUV) reticle inspection system using a thin film coating spectral purity filter (SPF) positioned on or proximate to the EUV imaging sensor. The present invention may be embodied in the thin film coating SPF, a reticle inspection system that includes the thin film coating SPF, as well as methods for making and using the thin film SPF in reticle inspection.

The EUV reticle inspection system may include a discharge produced plasma (DPP) or laser produced plasma (LPP) light source, a reticle illuminator for delivering light to the reticle, an objective for collecting reflected light and scattered light from the reticle, and a EUV imaging sensor. A set of illumination optics is located between the plasma light source and the reticle, while a set of objective optics is located between the reticle and the imaging sensor. A thin film coating SPF having desired spectral characteristics may be positioned or proximate to the imaging sensor. In one aspect of the invention, the SPF may be applied to the underside of the top window of the imaging sensor. In another aspect of the invention, the SPF may be located proximate to the imaging sensor in any position in the reflected light path between the reticle and the imaging sensor. For example, the SPF may be located on a mirror or window in the objective physically separated from the imaging sensor. The thin film filter positioned in the reflected light path may be the only spectral purity filter in the system, eliminating the need for any other SPF in the system. Alternatively, the reticle inspection system may include a thin film SPF positioned in the reflected light path in addition to a second SPF positioned in the incident light path.

The spectral characteristics of the thin film SPF include a band-pass characteristic in a region around 13.5 nm. The SPF also attenuates at least a portion of the 100-1200 nm spectral range below 90% of the nominal transmissivity of the filter at 13.5 nm. In a particular embodiment of the invention, the spectral characteristics may include a band-pass characteristic at 13.5 and attenuation of the 100-1200 nm spectral range below 90% of the nominal transmissivity of the filter at 13.5 nm.

The invention contemplates configuration of the thin film coating as a single element coating or a single compound coating. In addition, multiple layers of single element and/or single compound layers may be combined to create a multi-layer thin film filter. In a particular embodiment, the thin film coating includes Zirconium (Zr), or Silicon-Zirconium (Si/Zr) in a thin film coating having a thickness substantially between 10 nm and 100 nm. The thin film coating may also include Beryllium (Be), Boron (B), Magnesium (Mg), Aluminum (Al), Silicon (Si), Yttrium (Y), Niobium (Nb), Molybdenum (Mo), Technetium (Tc), Ruthenium (Ru), Rhodium (Ru), Molybdenum-Silicon (Mo/Si), Silicon Carbide (SiC) or Silicon Nitride (Si3N4) or any other suitable elements or compounds.

In view of the foregoing, it will be appreciated that the present invention significantly improves upon prior reticle inspection systems. Specific structures and processes for implementing the invention, and thereby accomplishing the advantages described above, will become apparent from the following detailed description of the illustrative embodiments of the invention and the appended drawings and claims. It is to be understood that both the foregoing general description and the following detailed description are exemplary and explanatory only and are not necessarily restrictive of the invention as claimed. The accompanying drawings illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE PREFERRED EMBODIMENTS

Reference will now be made in detail to the subject matter disclosed, which is illustrated in the accompanying drawings. As an illustrative example, the present invention may be embodied in a discharge produced plasma (DPP) or laser produced plasma (LPP) extreme ultraviolet (EUV) reticle inspection system that includes a thin film coating spectral purity filter (SPF) positioned on or proximate to the EUV imaging sensor. The invention includes any optic component carrying the film coating SPF located proximate to the EUV imaging sensor, which includes any optic component located in the reflected light path in a EUV reticle inspection system. The invention specifically contemplates applying the SPF directly to the EUV imaging sensor, such as a thin film coating SPF deposited on the underside of the top window of the imaging sensor. The invention further includes methods for making and using the SPF in reticle inspection systems.

It is recognized herein that configuring the SPF as a thin film coating positioned on or proximate to the imaging sensor significantly improves over prior SPF assemblies. Specifically, configuring the SPF as a coating positioned on or proximate to the EUV imaging sensor produces at least the following advantages: (a) prevents stray light from entering the image sensor; (b) avoids the need for a separate support structure for the filter; (c) provides a stronger and more durable support for the filter than the mesh-like support structures used in prior SPF design; (d) improves the transmission efficiency of the filter by eliminating the shadow caused by the mesh-like support; and (e) greatly increases the life of the filter.

Figure 1:
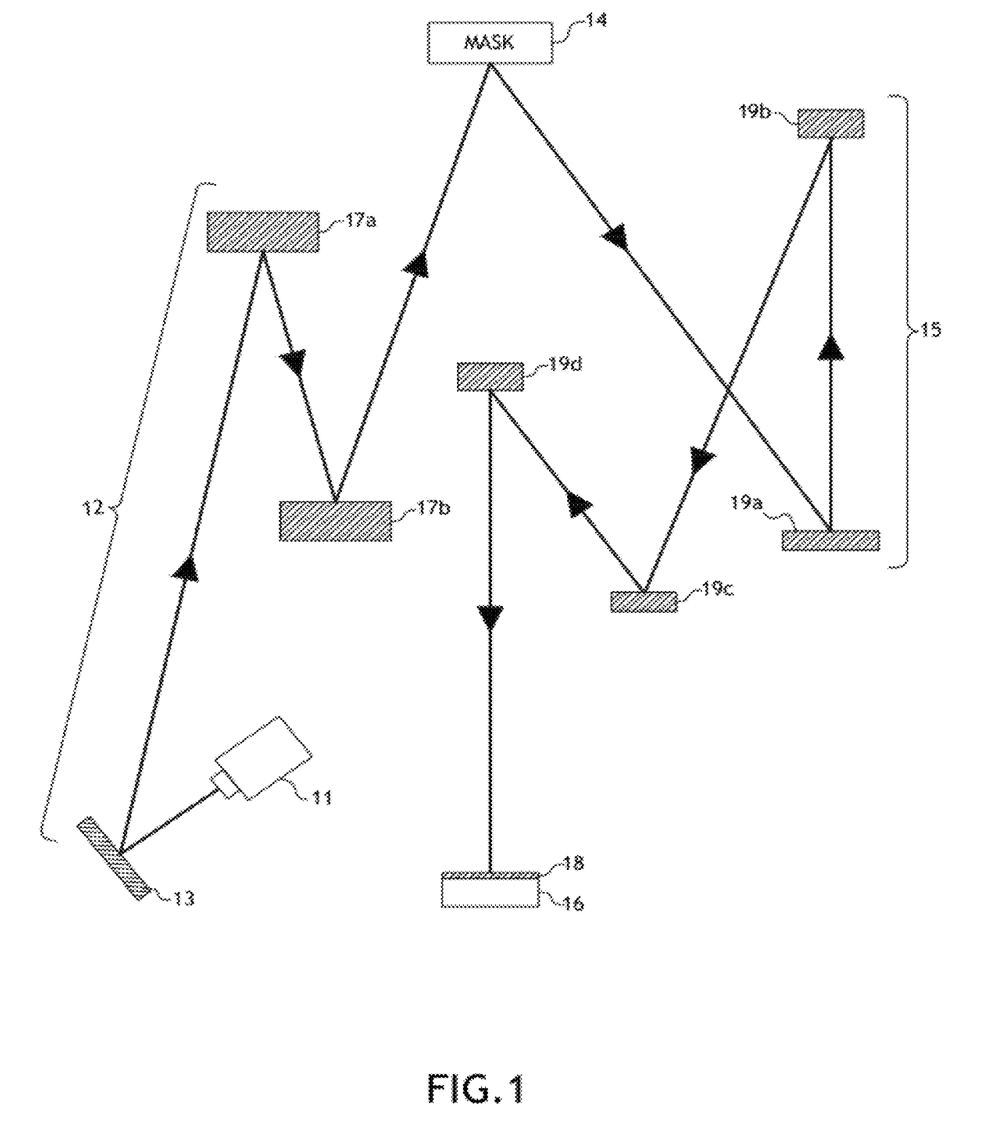
FIG. 1 is a schematic diagram of the EUV reticle inspection system including a thin film coating SPF located on the EUV imaging sensor.

According to one aspect of the invention, FIG. 1 is a schematic block diagram of an improved EUV reticle inspection system 10 using a thin film coating SPF carried directly on the EUV imaging sensor 16. The EUV reticle inspection system 10 includes a EUV light source 11 that generates EUV light for reticle inspection. The EUV light source 11 can be either laser produced plasma (LPP) or discharge produced plasma (DPP) source. An LPP source typically includes a laser (e.g., $CO_2$ or YAG laser) directed into a vacuum chamber containing an ionization target, such as Xenon (Xe) or Tin (Sn), where the laser energy ionizes the gas into plasma. The ionization laser is typically about 1 μm or 10 μm in wavelength and ionization of the gas to plasma releases the desired 13.5 nm EUV light. A DPP source typically includes a chamber containing an ionization target (Xe or Sn), and the plasma is generated via high pulsed voltage or current. The system 10 also includes illumination optics 12 and a reticle illumination position for receiving a reticle 14 for inspection. The illumination optics 12 may include a series of condensing mirrors 17a and 17b configured to condense the EUV illumination into a narrow beam directed to the reticle illumination position. The reticle 14 is printed with an absorber that defines absorptive traces and reflective regions that reflect the 13.5 nm EUV light. During wafer production, the reflective portions of the reticle not covered with the absorber reflect the EUV light onto a wafer to expose the integrated circuit into the wafer. For inspection purposes, the EUV light is reflected or scattered into the EUV imaging sensor 16, which captures an image of the reticle for inspection.

In another aspect of the invention, the EUV reticle inspection system 10 includes objective optics 15 located between the reticle illumination position and the EUV imaging sensor 16. The objective optics 15 may include a series of mirrors 19a, 19b, 19c, and 19d arranged to collect the reflected or scattered light from the reticle 14 and form an image of the reticle at the image sensor 16. In another aspect of the invention, the thin film coating may be applied directly to the top surface of the EUV imaging sensor or to a separate window that is positioned next to or fits over the top surface of the EUV imaging sensor. In particular, the SPF 18 may be applied to the underside of the top surface of the imaging sensor 16.

Figure 2:
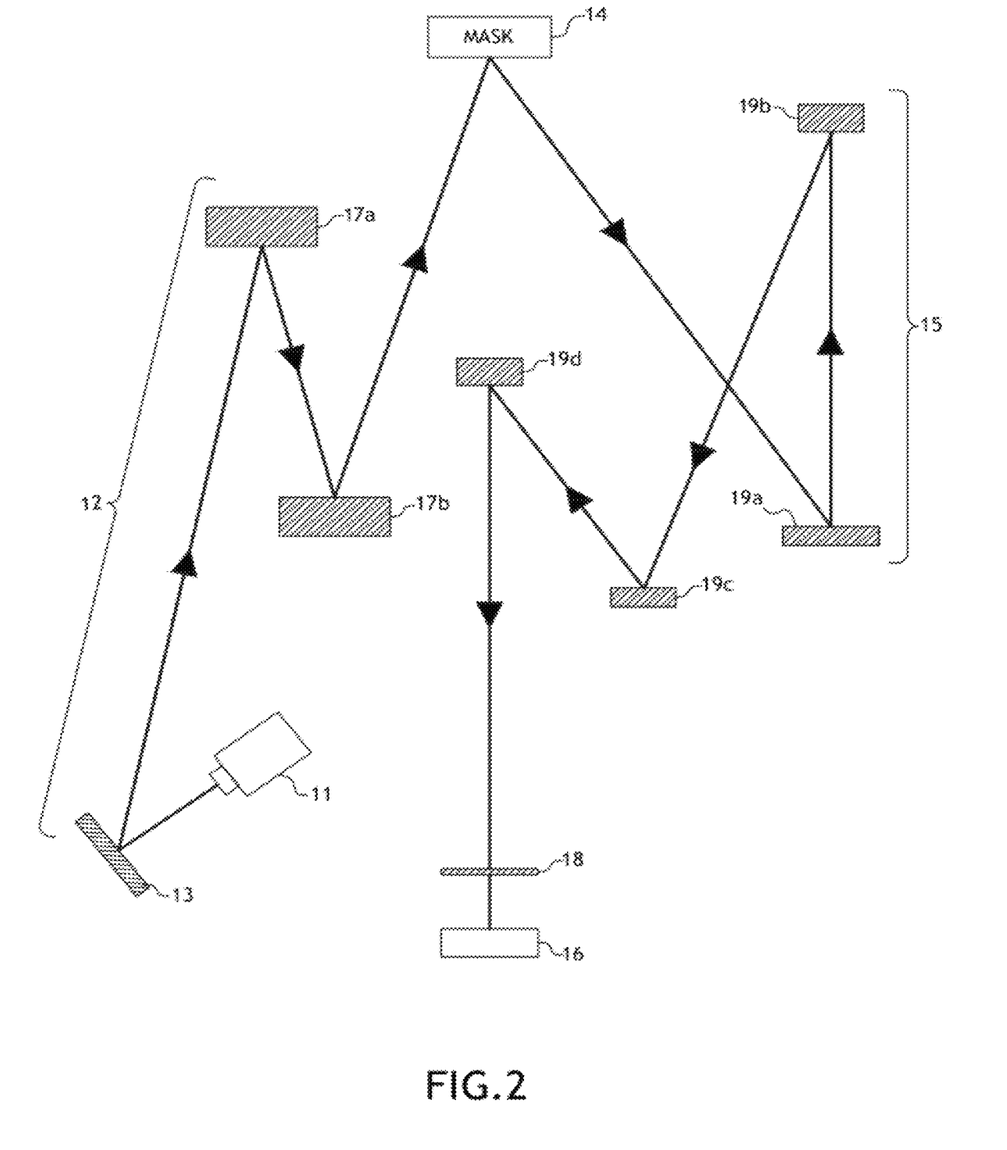
FIG. 2 is a schematic diagram of the EUV reticle inspection system including a thin film coating SPF located proximate to the EUV imaging sensor.

FIG. 2 is a schematic block diagram of an alternative configuration of the EUV reticle inspection system 10 in which the film coating SPF 18 is located proximate to but not directly on the EUV imaging sensor 16. For example, the SPF 18 may be located on a separate window, on a mirror, or in another suitable location in the objective optics 15. While locating the SPF directly on the imaging sensor 16 provides the advantages of using the imaging sensor to serve as the physical support for the filter, locating the SPF 18 in another location proximate to the imaging sensor in any location on the objective side of the reticle accomplishes the important advantages accomplished by locating the SPF in the reflected light path.

Locating the SPF 18 in the reflected light path on the EUV imaging sensor, after the illumination optics 12 and the objective optics 15, produces the previously described advantages over the conventional systems. In summary, these advantages include preventing stray light from entering the system between the SPF and the EUV imaging sensor and avoiding the need for a separate support structure for the filter. The imaging sensor also provides a stronger and more durable support for the filter than the mesh-like support structures used in prior SPF design. Eliminating the mesh-like support structure also improves the transmission efficiency of the filter by eliminating the shadow caused by the mesh-like support. In addition, locating the SPF in the reflected light path rather than the incident light path greatly increases the life of the filter due to the lower thermal load and lower number of high energy ions or particles on the filter. These advantages are accentuated when the thin film SPF 18 is the only spectral purity filter needed for the system, and there is no need for any spectral purity filter in the incident light path.

The thin film coating SPF 18 in the reflected light path, positioned on or proximate to the EUV imaging sensor 16, may be the only spectral purity filter in the system, eliminating the need for any filter in the incident light path. This configuration is particularly advantageous when the EUV light source 11 does not generate significant energy outside the 10-70 nm range, which allows all of the spectral purity filter objectives to be cost effectively met with a single thin film coating filter located in the reflected light path. Recognizing that at least some EUV light sources do not produce significant optical energy outside the 10-70 nm range was an important development in the development of EUV inspection technology because this revealed that any advantages attained by the conventional approach of locating the SPF in the incident light path were more than offset by the drawbacks on this approach. This opened the way to the completely new approach of configuring the SPF as a lower cost, more effective thin film coating filter located in the reflected light path.

In some cases, some type of spectral purity filter may still be justified in the incident light path. Nevertheless, even in this case, it has been determined that at least the certain filtering functionality is more effectively shifted to a thin film filter positioned in the reflected light path, and preferably located directly on or proximate to the EUV imaging sensor. Specifically, a thin film can be advantageously used to attenuate light in the 100-1200 nm range. This accomplishes a major spectral purity filtering function with the thin film filter, while producing additional design flexibility through the cooperative design of two filters, a first thin film SPF positioned in the reflected light path along with a second SPF positioned in the incident light path, to meet the sometimes competing design objectives of spectral purity filtering.

Figure 3:
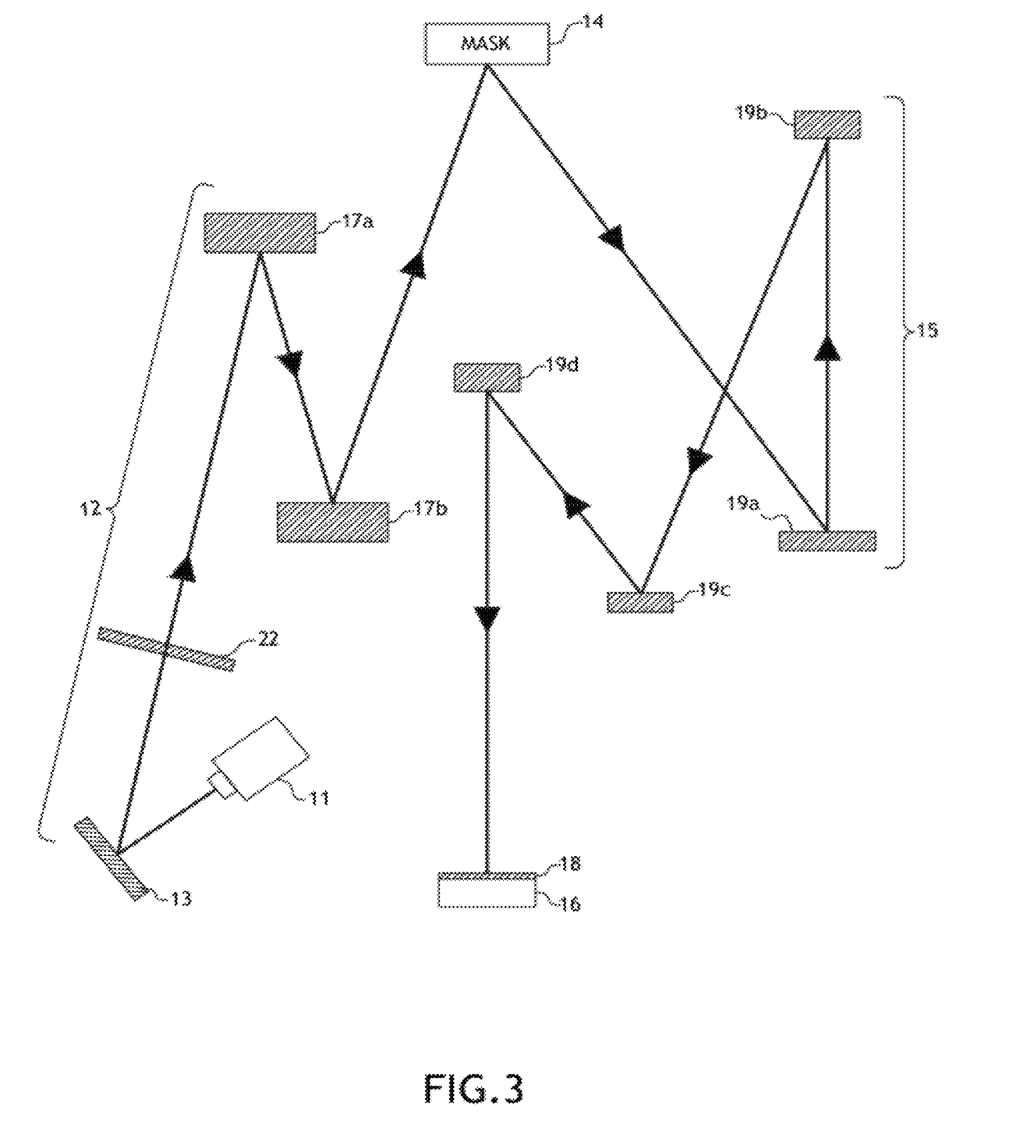
FIG. 3 is a schematic diagram of an alternative EUV reticle inspection system that includes a second spectral purity filter in addition to the thin film coating SPF located on the EUV imaging sensor.

FIG. 3 is a schematic diagram of an alternative EUV reticle inspection system 30 that includes a thin film coating SPF 18 located on the EUV imaging sensor 16 in addition to a second SPF 22 located in the incident light path between the EUV light source 11 and the reticle illumination position 14. In this alternative system, the two filters are designed to cooperatively meet the competing design objectives of spectral purity filtering. In particular, the thin film coating SPF 18 may be designed to provide the desired band-pass characteristic at 13.5 nm and attenuation within the 100-1200 nm spectral range, while the SPF 22 located in the incident light path may be designed to attenuate wavelengths below 10 nm, above 70 nm, or both. For example, the SPF 22 may be specifically designed to attenuate high frequency energy with wavelengths significantly below 10 nm that could be damaging to the illumination optics 12. As another design objective, the SPF 22 may be specifically designed to attenuate driver laser of LPP source with wavelengths in the 1-10 um range that could degrade the reticle image or damage the optics or reticle. The ability to specifically design the SPF 22 to meet these or other particular design objectives is facilitated by accomplishing the 100-1200 nm attenuation function with the thin film SPF 18 positioned on or proximate to the EUV imaging sensor 16.

Figure 4A:
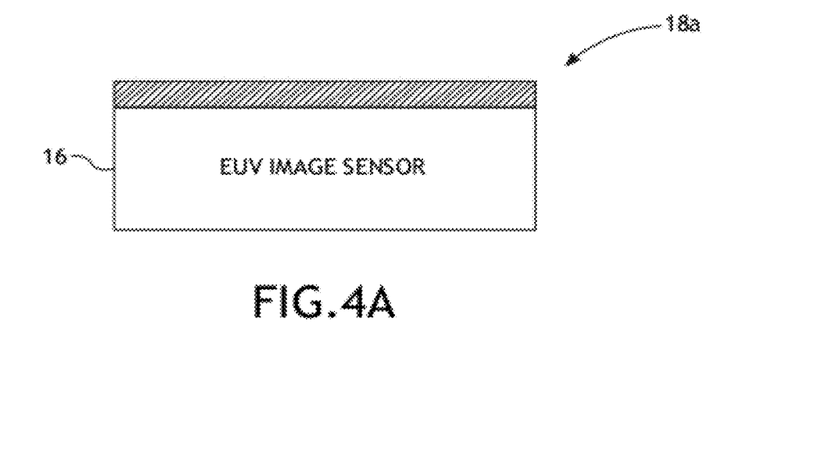
FIG. 4A is a conceptual illustration of the EUV imaging sensor carrying a single layer, single element SPF.
Figure 4B:
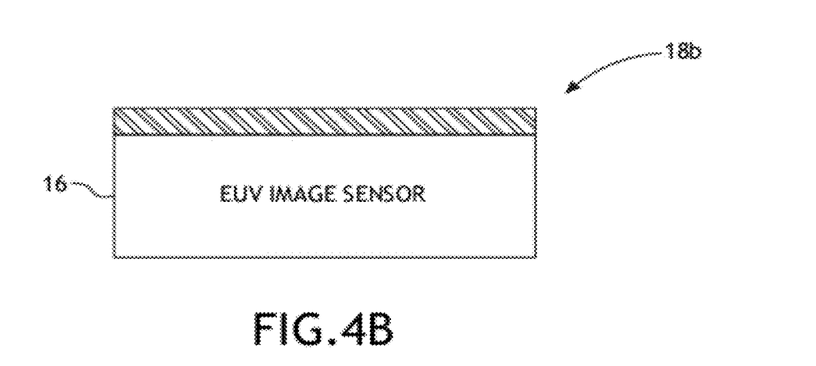
FIG. 4B is a conceptual illustration of the EUV imaging sensor carrying a single layer, single compound SPF.
Figure 4C:
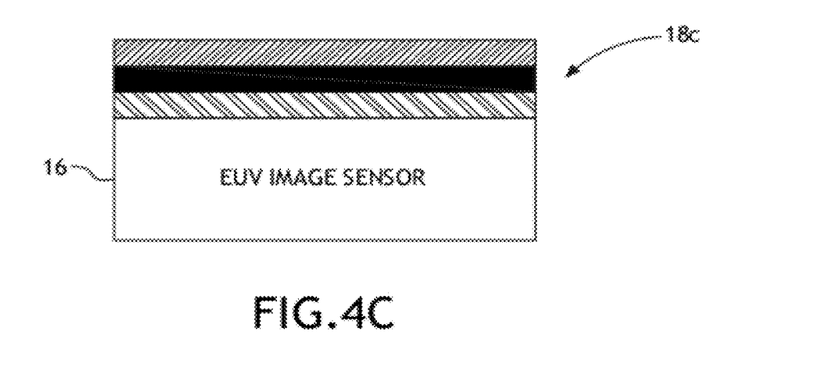
FIG. 4C is a conceptual illustration of the EUV imaging sensor carrying a multi-layer SPF.

According to various aspects of the invention, the SPF thin film coating may be composed of a single layer or multiple layers. Each layer typically includes a single element or a single compound and various combinations of elements and/or compounds may be applied to the imaging sensor in multiple layers. FIG. 4A is a conceptual illustration of a EUV imaging sensor 16 carrying a single layer, single element coating 18a. FIG. 4B is a conceptual illustration of the EUV imaging sensor 16 carrying a single layer, single compound coating 18b. FIG. 4C is a conceptual illustration of the EUV imaging sensor carrying a coating 18c consisting of multiple layers in which each layer typically includes a single element or compound.

Figure 5A:
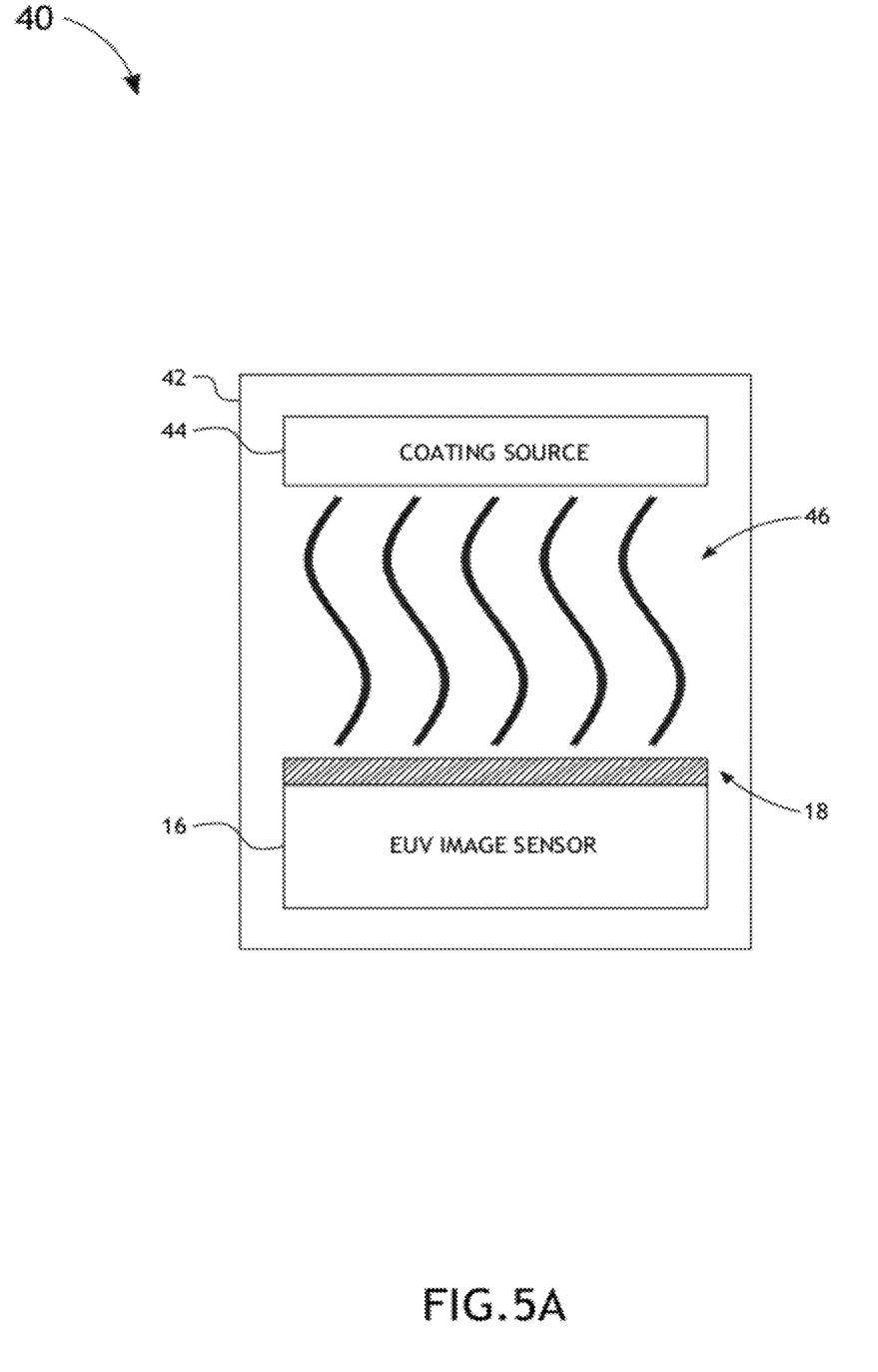
FIG. 5A is a conceptual illustration of a machine for applying the thin film coating SPF to the EUV imaging sensor.

FIG. 5A illustrates a conceptual illustration of a machine 40 for applying the thin film coating 18 to the EUV imaging sensor 16. According to one aspect of the invention, the thin film coating may be applied directly to the imaging sensor in any manner suitable for the particular coating selected. For example, the thin film coating may be deposited onto the imaging sensor 16 using deposition techniques such as, but not limited to, chemical vapor deposition (CVP), physical vapor deposition (PVD), evaporation deposition, molecular beam epitaxy (MBE), ion-beam sputtering, or any other suitable film coating technology currently existing or developed in the future. In a particular embodiment of the invention, the SPF 18 may be applied to the underside of the top surface of the imaging sensor 16. The system includes a vacuum chamber 42 and a coating source 44. The coating is applied within the vacuum chamber to avoid the introduction of impurities into the coating. The EUV imaging sensor is placed in the vacuum chamber 42 and the coating source 44 is activated in any suitable manner, typically by heating, irradiating or exposing the coating source to an electric or magnetic field. Activation causes the coating supply to sublimate, vaporize, evaporate, ionize, plasmatize, or otherwise form a material flow 46 that travels to and coats the EUV imaging sensor 16. The process is repeated for each layer to create the SPF 18. Additional thin film materials and coating technologies may also be employed as currently existing and developed in the future.

Figure 5B:
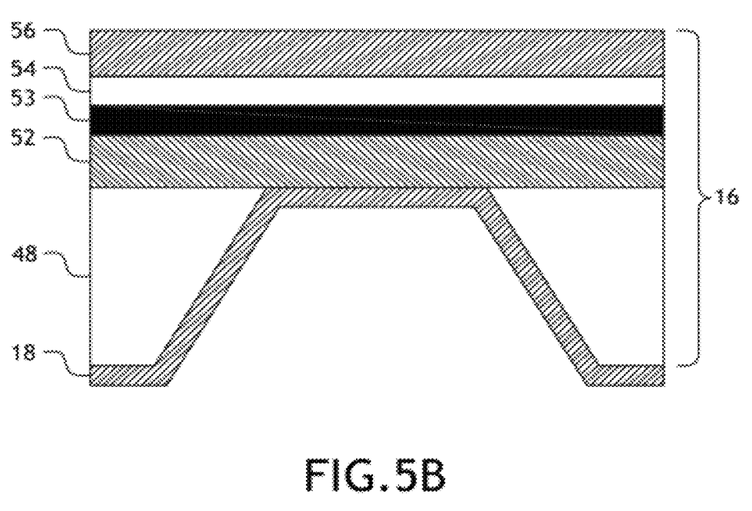
FIG. 5B is a schematic view of an imaging sensor equipped with a thin film coating SPF.
Figure 5C:
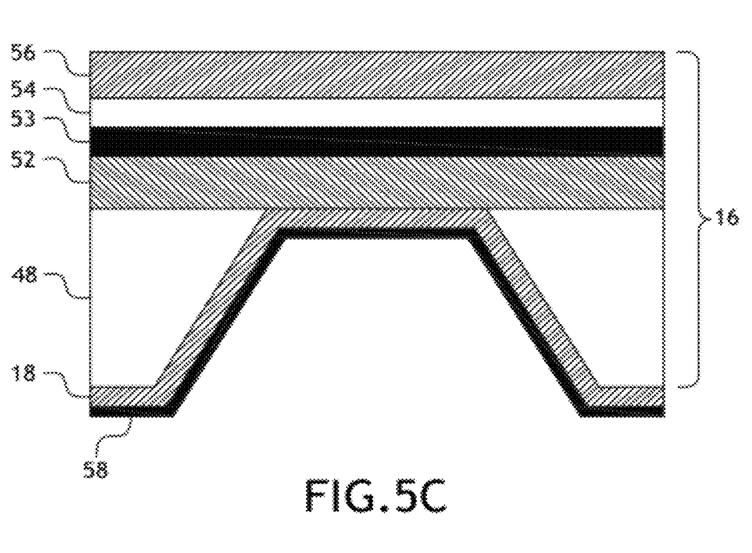
FIG. 5C is a schematic view of an imaging sensor equipped with a thin film coating SPF and an additional layer of material disposed upon the SPF.

FIGS. 5B and 5C illustrate a schematic view of an image sensor 16 following deposition of the thin film SPF filter 18, in accordance with one embodiment of the present invention. As shown in FIG. 5B, the imaging sensor 16 (e.g., CCD or TDI) may include a variety of functional layers. For example, the imaging sensor 16 may include a semiconductor substrate 48 (e.g., silicon), an epitaxial layer 52, a gate oxide layer 53, a gate layer 54 (e.g., $Si_3N_4$), and a layer of front side circuitry 56. In addition, while not shown, the imaging sensor 16 may further include one or more front side metal layers disposed on the front side circuitry layer 56. In one embodiment of the present invention, a thin film filter 18 may be deposited onto the back-thinned semiconductor substrate 48. It is noted herein that the back-thinning of the substrate 48 is depicted by the recessed portion of substrate 48, as depicted in FIGS. 5B and 5C. In this regard, the thin film layer 18 may be deposited onto the substrate 48 in any manner known in the art and as has been discussed previously herein. In a further embodiment, it is recognized that the imaging sensor 16 may undergo a back-side potential well engineering process prior to deposition of the thin film SPF 18.

In a further aspect, illustrated in FIG. 5C, an additional layer 58 of material may be deposited over the SPF 18. In one embodiment, the additional layer 58 may include a capping layer. It is noted herein that any capping material known in the art may be utilized as the capping layer 58 of the present invention. It is recognized, however, that the capping layer 58 need be transparent to the illumination desired for sensing. For example, in the case of sensing 13.5 nm wavelength light, the capping layer should at least be transparent to 13.5 nm wavelength light. In another embodiment, the additional layer 58 may include an additional SPF layer. In this regard, the additional layer may be utilized to filter additional portions of the electromagnetic spectrum not covered by the first SPF filter 18.

Figure 6:
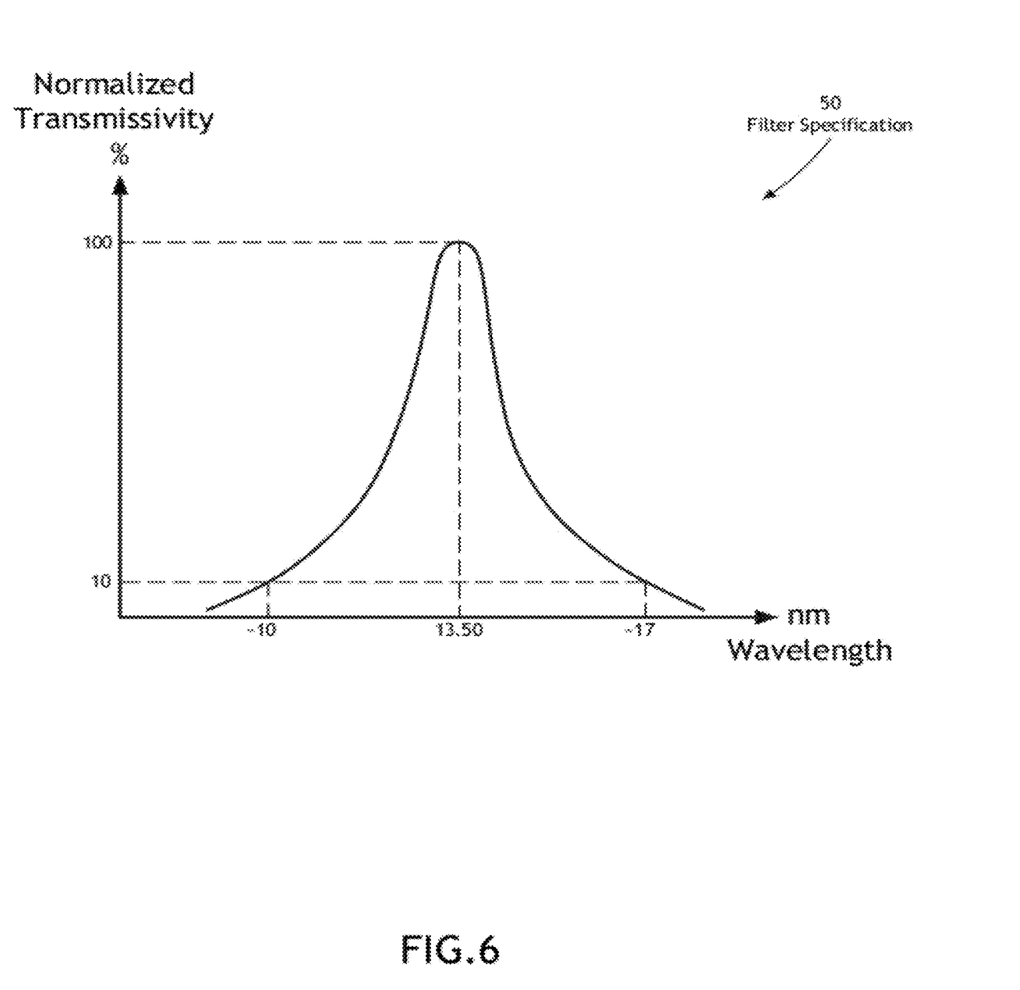
FIG. 6 is graph showing a suitable band pass filter characteristic for the thin film SPF.
Figure 7:
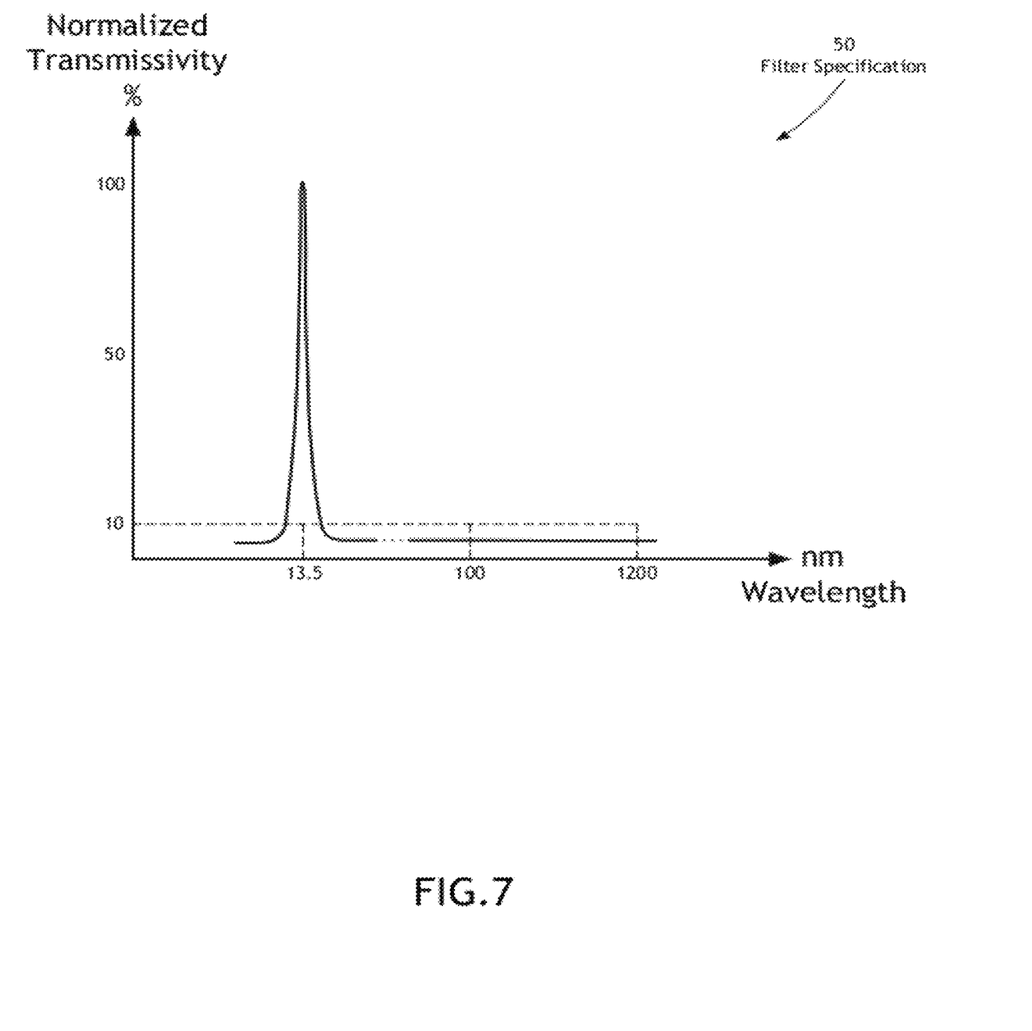
FIG. 7 shows the suitable band pass filter characteristic on a wider frequency scale.

FIG. 6 is a graph showing a band-pass filter characteristic 50 for the thin film SPF, in accordance with one embodiment of the present invention. FIG. 7 shows the pass filter characteristic 50 on a wider frequency scale. A suitable thin film SPF 18 has a band pass characteristic exhibiting high transmissivity in the spectral range of around 13.5 nm and significant attenuation within at least a portion of the 100-1200 nm spectral range. For example, the transmissivity of the SPF in at least a portion of the 100-1200 nm spectral range may be attenuated below 90% of the nominal transmissivity at 13.5 nm. Preferably, the entire spectral region from 100-1200 nm is attenuated below 90% of the nominal transmissivity at 13.5 nm, as shown in FIGS. 6 and 7. It should be noted that the bandwidth of the band pass filter characteristic 50 within the 10-70 nm range is not particularly critical because the Mo—Si multilayer coating on the illuminator and objective mirrors absorbs light in the frequency range of about 10-70 nm outside a narrow band around 13.5 nm. It is therefore sufficient for the band pass characteristic to fall generally within the range of about 10-70 nm provide that it exhibits a high transmissivity at 13.5 nm and the desired attenuation within the 100-1200 nm spectral range.

According to another aspect of the invention, zirconium (Zr) and silicon-zirconium (Si/Zr) with a coating thickness between 10 nm and 100 nm have been found to be suitable SPF coating materials meeting this filter characteristic. It is noted herein that other elements or compounds, individually or in combination, may be substituted for or combined with these coating to produce a filter with the desired spectral characteristics. In one embodiment of the invention, the coating materials include zirconium (Zr) or silicon-zirconium (Si/Zr), which have been found to impart the desired filter characteristic. In additional embodiments, the coating materials may include Beryllium (Be), Boron (B), Magnesium (Mg), Aluminum (Al), Silicon (Si), Yttrium (Y), Niobium (Nb), Molybdenum (Mo), Technetium (Tc), Ruthenium (Ru), Rhodium (Rh), or other suitable elements. Additional coating compounds may include Molybdenum-Silicon (Mo/Si), Silicon Carbide (SiC), Silicon Nitride (Si3N4) and other suitable compounds. It will be understood that the specific filter parameters and coatings described above are only illustrative and may be varied or refined somewhat while still achieving the objectives of the invention.

In view of the foregoing, the present invention provides an improved reticle inspection system reflecting an improved balance of design objectives, achieved by configuring an SPF as a thin film coating positioned on or proximate to the EUV imaging sensor. More specifically, the concern for protection of the objective optics primarily arises from concern with degradation caused by out-of-band light having a wavelength in the 100-1200 nm range. An examination of the spectrum produced by typical EUV light sources, however, reveals only insignificant levels of out-of-band light with a wavelength between 100 and 1200 nm, which is not excessively damaging to the objective optics. Moreover, only a small fraction (e.g., <10%) of the optical energy occurs at a wavelength greater than 120 nm. It has been further determined that almost all of the out-of-band light energy emitted by a typical EUV light source is in the 10-70 nm range, which is effectively filtered by the Mo—Si multilayers of the reticle and/or mirrors of the optical system. The determination that all or a portion of the SPF functionality can be moved to the reflected light path allows the filter to be configured as a thin film coating placed directly on or proximate to the EUV image sensor, which produces a number of important advantages.

In comparison to the conventional SPF located in the incident light path, the thin film SPF located in the reflected light path is not subjected to the fast ions and particles from the source, which significantly extends the life of the filter. By using the EUV imaging sensor itself as the supporting structure for the thin film filter, the filter can be made much thinner and still be sufficiently robust. The much thinner filter absorbs less EUV light, thus increasing system light throughput. The result is a much thinner film filter with a much longer lifetime due to the lower thermal load, lower contamination, and more robust support provided by the EUV sensor. In addition, the thin film filter also blocks substantially all stray light of DUV-IR wavelength from reaching imaging sensor. In contrast, significant amounts of stray light including DUV-IR wavelength light can enter the conventional system due to the extended physical separation between the spectral filter and the image sensor.

Locating the thin film filter directly on the EUV image sensor is also cleaner than a conventional separate thin film filter because the conventional thin film filter can break easily and generate particles that contaminate the optic elements. The lower thermal load on the thin film filter also makes the filter less susceptible to carbon contamination or oxidation, which would require plasma cleaning not possible on a conventional thin film filter. The tool uptime is therefore increased and maintenance downtime is decreased, with greater light throughput and improved image quality, by utilizing the thin film filter located directly in the EUV image sensor.

The subject matter described above sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

In view of the foregoing, it will be appreciated that present invention provides significant improvements in EUV reticle inspection for integrated circuit fabrication. Those skilled in the art will understand the many modifications and adaptations of the specific methods and systems described above may be implemented within the spirit and scope of the invention as defined by the following claims.

The invention claimed is:

1. An extreme ultraviolet reticle inspection apparatus, comprising:
    an extreme ultraviolet imaging sensor; and
    a thin film coating spectral purity filter having one or more selected spectral characteristics disposed on a back-thinned semiconductor substrate of the extreme ultraviolet imaging sensor imaging sensor, the extreme ultraviolet imaging sensor serving as a support structure for the thin film coating spectral purity filter.

2. The apparatus of claim 1, wherein the thin film coating spectral purity filter is configured for location in a reflected light path between a reticle under inspection and the imaging sensor, further comprising a second spectral purity filter configured for location in an incident light path between a discharge produced plasma light source and the reticle under inspection.

3. The apparatus of claim 1, wherein the one or more selected spectral characteristics include a band-pass characteristic substantially at 13.5 nm.

4. The apparatus of claim 3, wherein the one or more selected spectral characteristics further include a band-pass characteristic including at least 13.5 nm and at least a portion of a 100-1200 nm spectral range attenuated below 90% of nominal transmissivity at 13.5 nm.

5. The apparatus of claim 4, wherein the one or more selected spectral characteristics further include attenuation of the 100-1200 nm spectral range below 90% of the nominal transmissivity at 13.5 nm.

6. The apparatus of claim 1, wherein the thin film coating comprises a single layer thin film.

7. The apparatus of claim 1, wherein the thin film coating comprises a multi-layer thin film.

8. The apparatus of claim 1, wherein the thin film coating comprises one or more of Zirconium (Zr) or Silicon-Zirconium (Si/Zr).

9. The apparatus of claim 8, wherein the thin film coating has a thickness substantially between 10-100 nm.

10. The apparatus of claim 1, wherein the thin film coating comprises one or more of Beryllium (Be), Boron (B), Magnesium (Mg), Aluminum (Al), Silicon (Si), Yttrium (Y), Niobium (Nb), Molybdenum (Mo), Technetium (Tc), Ruthenium (Ru), Rhodium (Rh).

11. The apparatus of claim 1, wherein the thin film coating comprises one or more of Molybdenum-Silicon (Mo/Si), Silicon Carbide (SiC) or Silicon Nitride ($Si_3N_4$).

12. An extreme ultraviolet reticle inspection system comprising:
   an extreme ultraviolet light source;
   a reticle illumination position for receiving a reticle for inspection;
   an extreme ultraviolet imaging sensor;
   a set of illumination optics located between the extreme ultraviolet light source and the reticle illumination position;
   a set of objective optics located between the reticle illumination position and the imaging sensor; and
   a thin film coating spectral purity filter having one or more selected spectral characteristics disposed on a back-thinned semiconductor substrate of the extreme ultraviolet imaging sensor imaging sensor, the extreme ultraviolet imaging sensor serving as a support structure for the thin film coating spectral purity filter.

13. The system of claim 12, wherein the extreme ultraviolet light source comprises at least one of a discharge produced plasma (DPP) light source or a laser produced plasma (LPP) light source.

14. The system of claim 12, wherein the one or more selected spectral characteristics include a band-pass characteristic substantially at 13.5 nm.

15. The system of claim 14, wherein the one or more selected spectral characteristics further include a band-pass characteristic including at least 13.5 and at least a portion of a 100-1200 nm spectral range attenuated below 90% of nominal transmissivity at 13.5 nm.

16. The system of claim 15, wherein the one or more selected spectral characteristics further include attenuation of the 100-1200 nm spectral range below 90% of the nominal transmissivity at 13.5 nm.

17. The system of claim 12, wherein the thin film coating consists of single layer consisting essentially of a single element.

18. The system of claim 12, wherein the thin film coating consists of a single layer consisting essentially of a single compound.

19. The system of claim 12, wherein the thin film coating consists of multiple layers, each layer consisting essentially of a single element or a single compound.

20. The system of claim 12, wherein the thin film coating comprises one or more of Zirconium (Zr) or Silicon-Zirconium (Si/Zr).

21. The system of claim 20, wherein the thin film coating has a thickness substantially between 10 nm and 100 nm.

22. The system of claim 12, wherein the thin film coating comprises one or more of Beryllium (Be), Boron (B), Magnesium (Mg), Aluminum (Al), Silicon (Si), Yttrium (Y), Niobium (Nb), Molybdenum (Mo), Technetium (Tc), Ruthenium (Ru), Rhodium (Rh).

23. The system of claim 12, wherein the thin film coating comprises one or more of Molybdenum-Silicon (Mo/Si), Silicon Carbide (SiC) or Silicon Nitride ($Si_3N_4$).

24. The system of claim 12, further comprising a second spectral purity filter positioned between the extreme ultraviolet light source and the reticle illumination position.

25. A method for inspecting an extreme ultraviolet reticle, comprising:
   generating extreme ultraviolet light utilizing an extreme ultraviolet light source;
   directing the extreme ultraviolet light from the extreme ultraviolet light source to a reticle via a set of illumination optics;
   directing extreme ultraviolet light reflected from the reticle toward an extreme ultraviolet imaging sensor via a set of objective optics;
   filtering a portion of the extreme ultraviolet light reflected from the reticle with a thin film coating disposed on a back-thinned semiconductor substrate of the extreme ultraviolet imaging sensor imaging sensor, the extreme ultraviolet imaging sensor serving as a support structure for the thin film coating spectral purity filter, the thin film coating having one or more selected spectral characteristics; and
   receiving a portion of the light filtered by the thin film coating with the extreme ultraviolet imaging sensor imaging sensor.

* * * * *